United States Patent [19]

Lesur et al.

[11] Patent Number: 4,919,909
[45] Date of Patent: Apr. 24, 1990

[54] REACTOR FOR CATALYTIC SYNTHESIS AND PROCESS FOR USING THE REACTOR

[75] Inventors: Pierre Lesur, Paris; Christian Faury, Vanves; Guy Lafleur, Les Essarts; André Papillon, Saint-Maur-Des-Fosses, all of France

[73] Assignee: Societe Chimique de la Grande Paroisse, Paris, France

[21] Appl. No.: 145,631

[22] Filed: Jan. 7, 1988

Related U.S. Application Data

[63] Continuation of Ser. No. 804,505, Dec. 4, 1985, abandoned.

[51] Int. Cl.$^5$ .............................. C01C 1/04; B01J 8/02
[52] U.S. Cl. .................................. 423/360; 422/148; 422/202
[58] Field of Search ............... 422/148, 205, 190, 193, 422/202; 423/359, 360, 361

[56] References Cited

U.S. PATENT DOCUMENTS

| | | | |
|---|---|---|---|
| 2,847,284 | 8/1958 | Busey | 422/205 |
| 4,357,305 | 11/1982 | Loo | 422/202 X |
| 4,452,760 | 6/1984 | Peterson et al. | 422/148 |
| 4,552,724 | 11/1985 | Matsumoto et al. | 422/205 |
| 4,650,651 | 3/1987 | Fuderer | 422/202 X |
| 4,714,592 | 12/1987 | Zanma et al. | 422/202 X |

FOREIGN PATENT DOCUMENTS 911490 of 1954 Fed. Rep. of Germany.
2183985 of 1973 France.

Primary Examiner—Barry S. Richman
Assistant Examiner—Jill Johnston
Attorney, Agent, or Firm—Browdy and Neimark

[57] ABSTRACT

A reactor for single-layer, exothermic catalytic synthesis in the gaseous phase under pressure, is made up of a main casing under high pressure, comprising a cylindrical part and two hemispherical ends containing an enclosure for the catalyst carrier, including a single catalyst layer concentric to the body of force and whose external wall is covered with an insulator, a space being located between the internal wall of the main casing under high pressure resting on a helical metal winding from one end of the casing to the other, said main casing under high pressure and the enclosure for the catalyst carrier being provided with means for introducing and withdrawing gas streams, located at the ends of the main axis and arranged facing each other on the hemispherical ends. The enclosure for the catalyst carrier furthermore is equipped with a vertical pipe for filling and emptying the catalyst. The reactor can be used for synthesizing ammonia and methanol.

21 Claims, 2 Drawing Sheets

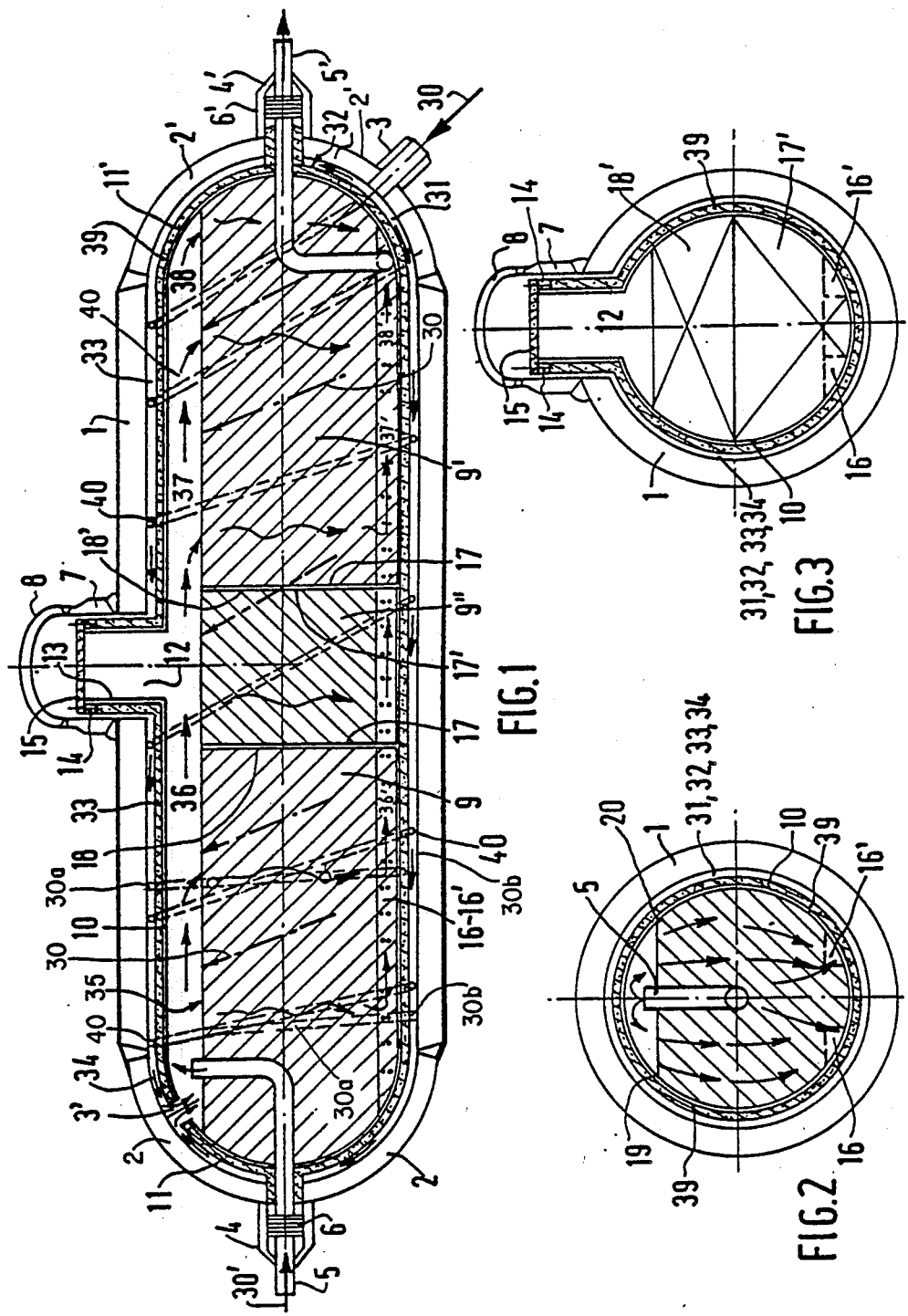

REACTOR FOR CATALYTIC SYNTHESIS AND PROCESS FOR USING THE REACTOR

This application is a continuation, of application Ser. No. 804,505, filed Dec. 4, 1985, now abandoned.

FIELD OF THE INVENTION

The present invention relates to a process for exothermic catalytic synthesis in a gaseous phase under pressure and, more specifically, to a type of horizontal reactor for such synthesis, particularly for the synthesis of ammonia from nitrogen and hydrogen, and the synthesis of methanol.

BACKGROUND OF THE INVENTION

For several decades exothermic catalytic balance reactions in a gaseous phase have been conducted in synthesis reactors traditionally containing several layers of catalyst, between or among which were arranged the means of controlling and regulating the reaction temperatures. The cooling, either continuous within the catalytic compound or intermittent between layers, allows the reaction conditions to be separated from equilibrium conditions with resultant increase in the speed of the reaction.

The constraints imposed by economic conditions have driven research toward facilities whose purpose is to decrease the energy consumption of the synthesis loop or, more generally, the overall consumption of the installation manufacturing ammonia or methanol.

In particular, decreasing the pressure of the exothermic synthesis in the gaseous phase has been suggested, which leads to the construction of larger and larger installations.

Increasing the conversion rate has also been suggested. This rate can be increased by replacing the temperature control, done by quenching between catalytic beds, by one or more internal exchangers. The complicated mechanical design of such reactors causes a high expense and uncertain reliability, and the operations for loading and emptying of the catalyst are made more difficult. The most up-to-date multilayer reactors do not easily lend themselves to the introduction of one or more exchangers between the layers in addition to the outlet exchanger because of complexity and risk of internal leaks.

The conversion rate has also been increased by decreasing the particle size of the catalyst, which increases its activity but also its pressure drop.

The conversion rate has also been increased by increasing the volume of the reactor. Vertical reactors with axial circulation allow this to happen only to a limited extent, their pressure drop becoming prohibitive beyond about 70 m$^3$ of catalyst. Vertical reactors with radial circulation as well as horizontal multilayer reactors with vertical circulation allow an increase in the volume of the catalyst by elongating the container without increasing the diameter. Radial multilayer reactors as well as many axial reactors present disadvantages involving reliability and risk of leaks due to an opening equal to the diameter of the pressure casing for introducing and withdrawing the internal equipment while the catalyst is being changed. It is difficult to make the wide-diameter flanges tight. The diameter is, in general, limited by that of the opening because of structural problems and the permissible size for transport. Furthermore, increasing the volume of the catalyst in multilayer radial and horizontal reactors leads to very long internal equipment, resulting in problems in construction, reliability and changing the catalyst.

Another disadvantage of multilayer reactors lies in the fact that their rate of filling: the ratio of the volume of the catalyst to the volume of the enclosed space under high pressure, minus the volume of the internal exchangers, is only about 0.5.

The development of technologies and economic conditions in the sector of mechanical design tends to make complex internal equipment made of stainless steel very expensive and, in contrast, the simple technique of so-called single layer containers, in series, is competitive. The latter uses only a large reactor but large or small vertical reactors containing a single layer of catalyst, in series, and connected to each other by piping, the exchangers being enclosed in separate containers. This technique does not present all the disadvantages of multilayer reactors, but it does not easily lend itself to using large volumes of catalyst since the pressure drop increases rapidly due to the axial circulation of the gases. On the contrary, the single-layer horizontal reactors with vertical circulation are much better for use with large catalylic volumes.

As of 1944, at a time when ammonia was produced in low volume catalytic facilities, German Pat. No. 911,490 already proposed a horizontal reactor containing a single layer of catalyst in which the gases under high pressure and temperature of the reaction are in contact with the pressure casing. These operating conditions require the use of highly alloyed steels which are very difficult to use in wide diameters. This type of reactor is not transferrable to large synthesis units.

More recently, French Pat. No. 2,183,985 described a horizontal reactor for synthesizing ammonia with an internal-external vertical heat exchanger and two reaction chambers with catalyst layers. This vertical exchanger provides a heat exchange between the gas streams. This solution appears obviously complicated as far as internal equipment is concerned, it presents the disadvantages inherent in multilayer reactors of a high cost, marginal reliability and rather difficult handling of the catalyst with a limited filling rate.

SUMMARY OF THE INVENTION

An effort has been made to improve the technique of single layer containers by freeing them from their limits and constraints, by combining a very high conversion rate with a low pressure drop in the catalyst, regardless of the volume of the catalyst, all by turning to very simple and proven design techniques. These advantages are valid regardless of the size of the facility. The type of reactor suggested is compatible with lowering the synthesis pressure and increasing the volume of the catalyst consecutively up to about 100 to 150 m$^3$, for example. The design of the internal equipment, and the technologies of construction, assembly, handling of the catalyst and use without gas leaks are very simple.

The invention consists, in the design of synthesis reactors, not provided with internal exchangers, whose walls under high pressure are not heated to very high temperatures by the gas in contact therewith, if they are of the cylindrical, horizontal, single-layer type. Thus, the walls do not contribute to the flow. This result, obtained without complicating the circulation circuit of the gases in the reactor unit, allows the computational temperature of the pressure casing sleeve to be decreased from 550° C. to 450° C., or even 300° C. and lower depending on individual cases. At the start of the facility it is usually necessary to introduce, at the moment of start-up, synthesis gas into the catalytic chamber at a temperature which can approach 500° C. and the temperature of the effluent gas from the catalytic layer can slightly exceed 500° C. The present technique avoids having the two very hot gas streams come into contact with the casing under pressure.

The main object of the invention is to provide an apparatus and a process for synthesis using exothermic heterogenous catalysis in gaseous phase under pressure.

The horizontal cylindrical reactor with controlled wall temperature is mainly made up of a main casing under high pressure, or pressurized outer shell of a cylindrical part and two hemispherical ends containing a concentric inner shell defining an enclosed space for the catalyst carrier whose external wall is covered with an insulator. A space is provided between the internal wall of the language pressurized outer shell; and that of the external wall of the enclosed space for the catalyst carrier covered with an insulator, resting on a helical metallic winding extending from one end of the casing to the other, said winding resting itself on the internal wall of the outer casing. The main casing under high pressure and the enclosed space for the catalyst carrier are provided with means of introducing and withdrawing gas streams at the ends of the main axis. These means are arranged facing each other on the hemispherical ends and, furthermore, the enclosed space for the catalyst carrier is equipped with a vertical pipe for filling and emptying the catalyst.

According to the individual case, this type of reactor allows the use of a computational temperature of the pressure casing which is lower than or equal to 300° C., more on the order of 450° C., due to the thermal protection of the wall of the main pressure resistant casing.

The wall of the main outer casing under high pressure is protected thermally in two ways: on the one hand, by the insulating external covering of the internal catalyst-carrying container and, on the other hand, by an isothermic gas stream lower in temperature than the gas contained in the internal catalyst-carrying container, said isothermic gas circulating helically between the pressure wall and the wall covering with its insulation. This gas is none other than the reactive feed gas under pressure in the reactor.

The insulating external covering of the catalyst-carrying enclosed space has a resistance to compression under the operating conditions and presupposes the function of supporting the enclosed space by resting on the helical winding, which allows heat bridges between the helical winding and the pressure-resistant casing to be eliminated. The insulation is itself enclosed in mechanical protective casings, concentric in relation to the enclosed space for the catalyst-carrier, supported by circular ring supports, not shown, in which openings are provided which allow the passage of the protective gas of the pressure casing with helical circulation. Further, this insulation is advantageously inert and is not affected by water introduced while the catalyst is being emptied.

To keep the internal wall of the main casing at a temperature equal to or less than 300° C., a feed stream at about 200° C., 120°–250° C., is passed through the space provided between the casing under pressure and the internal enclosed space containing the catalyst, following a helical path from one end of the container to the other. This gas then leaves the reactor and is then reheated before being introduced into the catalytic space.

This gas cushion at 200° C. is almost isothermal because of the insulating covering of the enclosed space with the catalyst carrier. Additionally, the computational temperature of 300° C. makes it possible to use slightly alloyed steels, whose fabrication is simple, which operate very much below their elastic limit and are of moderate thickness.

According to a variant of the technique, and in order to simplify as much as possible the internal equipment of the equipment, the stream of protective gas is introduced into the space between the casing under pressure and the internal enclosed space after having been heated in an external exchanger to the temperature at which the reaction begins, for example 400° C. in the case of synthesizing ammonia. The circuit of the isothermal protective gas is the same as before, except that the gas does not leave the reactor but is introduced directly into the enclosed space with the catalyst carrier between 370° and 420° C. Since this internal enclosed space is always covered on the outside by insulation so that the gaseous layer is kept at about 400° C., the computational temperature of the casing under pressure can thus be about 450° C., whereas the gas passing through the catalytic enclosure may attain 500° C.

Structural steels are less alloyed than if the computational temperature was about 550° C. as in other types of reactors and they function even more below their elastic limit; the thickness of the wall under pressure thus remains reasonable and its use is easy.

In these two types of operation, the steels are subjected to conditions far removed from those of hot corrosion by hydrogen.

Further, to avoid any contact with the pressure casing, the very hot gas from the start of the reaction is introduced into the catalytic chamber either by the intermediate step of a box resistant to high pressure but small in diameter and heatinsulated on the inside, or by using internal piping. In the same way the very hot effluent gas from the catalytic chamber is removed either by the intermediate step of a box with the same characteristics as the one above or by using internal piping.

In this type of adiabatic chemical reactor, suited for exothermic reactions under high pressure in gaseous phase and using heterogenous catalysis, the reaction gases circulate vertically downward or upward through the catalytic bed. The shape of the reactor and the direction of the gas circulation in the catalyst zone, in relation to the axis of the reaction space are adapted to the volume of the catalyst to increase the cross section of flow of the gas through the catalyst and thus to decrease greatly the pressure drop and therefore allow the use of a very small-grained catalyst.

The reagents and the effluents are routed by two internal pipes through two distribution pipes which provide a good distribution of the gas in the catalytic mass. Inside the enclosed space with the catalyst carrier, in its lower part, two gas-collecting pipes are located which are connected to the piping of the effluent reaction gas.

Insertion and withdrawal of the large amount of catalyst are effected through the opening in the upper part of the catalytic chamber, preferably in the center of it, corresponding to a piping or internal casing welded to the main casing of the enclosed space. These operations of inserting or removing the used catalyst are made possible by at least two vertically removable internal partitions, made of at least two sectors of a circle which fit into each other and which provide, temporarily, a work space between them. This also allows the catalyst to be made even at a distance from the enclosed end of the space.

Due to this method of filling, this type of horizontal reactor is well suited to high and very high-volume catalytic layers.

The rate of filling of these single-layer horizontal reactors is very high, on the order of 0.7 to 0.9.

The operations for handling the catalyst are simplified and the lifting machinery is of very modest range and power. Actually, since the internal equipment is put into the reactor during its construction it is never necessary, even when assembling on site, to insert or remove the catalyst-carrying pan, or even the complete internal equipment. The risks of hydrogen leaks can be avoided by using, a filling and emptying orifice of the catalyser of small diameter and covered by a welded cover which can be cut out, or with a flanged cover of small diameter preferably welded. Since changing the catalyst is a less and less frequent operation, it may be desirable to use a welded cover.

The problems of longitudinal expansion are solved by vertically welding the internal casing, where the catalyst is introduced, on the main casing of the catalytic space with this internal casing being equipped with means such as bolts diametrically opposite each other which allow a stationary point by support-clamping on the body of force, this point not being stationary in relation to the vertical expansions which can occur freely.

Depending on the volumes of the catalyst, the conversion rate, the pressure drop and other specific technical and economic criteria, it is advantageous to propose a series of catalytic reactors each containing a single bed of catalyst with the reaction gases circulating vertically and not having an internal exchanger. These various associated reactors, in series or sometimes in parallel to one or several horizontal reactors, can be vertical or spherical. Several horizontal reactors in series can be envisaged, in general two or three or, for the volumes of catalyst currently in use, a first reactor which is either vertical or spherical, and a second horizontal reactor which can be followed by another horizontal reactor.

In a small installation with a low investment cost, the simplicity of the design would be desirable, without high energy recovery, two reactors in series can be used and, depending on the volumes of the catalyst, a first reactor, either vertical or spherical, and a second vertical, spherical or horizontal, reactor. Cooling between the reactors can be direct, that is, provided by quenching. Actually, the decrease in the conversion rate due to quenching, and the resulting increase in the size of the equipment of the synthesis loop, are largely compensated for by the absence of the intermediate exchanger made of stainless steel. The conversion rate is maintained at a high level by using a very small grain size. This is made possible by the shape of the reactors as seen above.

In contrast, in a large installation where the energy cost would be decisive, high-capacity reactors in series could be used and, possibly, in larger numbers (three or four in practice). Depending on the volumes of the catalyst, the first reactor(s) will be generally spherical or horizontal, with the nonhorizontal reactors being multilayer. The rate of conversion will be increased by using indirect cooling between layers, by heat exchange. Heat recovery can be optimized by using one or more high-pressure boilers for one or more of the effluents of the series reactors, the other effluents being cooled in heat exchangers by the gas feeding the first bed. This combination of reactors and other equipment thus allows a higher overall conversion rate. The overall pressure drop is less than in the present most productive multi or single-layer reactors.

Between these two extreme examples, all combinations of types of vertical, horizontal or spherical single-layer reactors are possible, with direct cooling by quenching or indirect cooling by heat exchange, with heat recovery of the reaction heat by one or more boilers or heating the high-pressure water and heat exchangers with the feed gas. This means that this technique allows perfect adaptation to whatever the technical and economic constraints there may be, with a high yield.

Below are given examples of nonlimiting embodiments of horizontal single-layer reactors of the type described in the invention, suited for the synthesis of ammonia and methanol. More specifically, in the following description the temperatures indicated and the terms synthesis or protective gas, gas after reaction or reactive effluent relate to the synthesis of ammonia. The type of reactor is compatible with all pressures and in practice it can be advantageously used between 50 and 350 bar.

BRIEF DESCRIPTION OF DRAWINGS

FIG. 1 shows a horizontal single-layer reactor according to the present invention.

FIG. 2 shows a section taken along line 2—2 of the reactor in FIG. 1.

FIG. 3 shows a section taken along line 3—3 of the reactor in FIG. 1.

DETAILED DESCRIPTION OF THE DRAWINGS

Example 1

Figure 4:
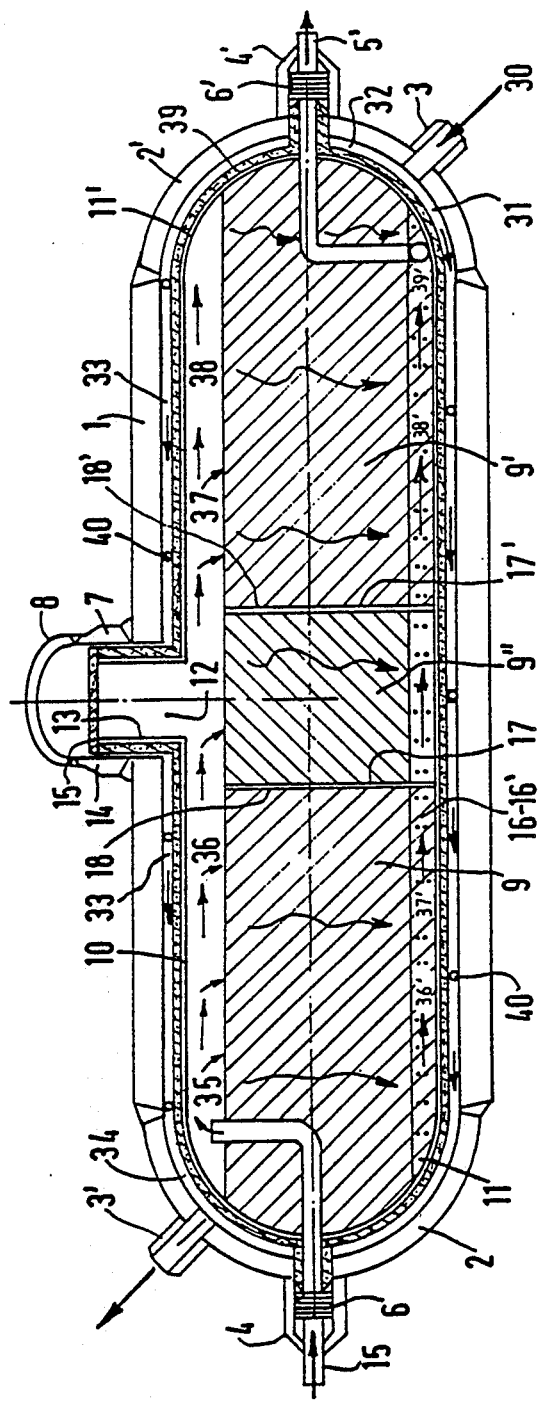
FIG. 4 shows a horizontal single-layer reactor with a controlled wall temperature of a very moderate level.

Horizontal single-layer reactor with a wall temperature controlled at a level of about 400° C., represented in FIGS. 1,2 and 3 of the accompanying drawing.

The body of the reactor is made up of a steel casing or a Pressurized shell (1) and two hemispherical ends made of the same type of steel (2) and (2').

End (2') is equipped with a pipe (3) for introducing the synthesis or protective gas, preheated to 400° C. maximum, and used for maintaining the body of force at a temperature lower than that of the catalytic chamber, with a pipe (4') forming a thermal casing and a box for the compensators (6') of the horizontal axial pipe for the discharge of the hot effluent synthesis gas (5') at a temperature of about 500° C., between 450° and 530° C.

End (2) is equipped with a pipe (4) which forms a thermal casing and a box for the compensators (6) of the axial horizontal inlet pipe (5), located diametrically opposite pipe (5'), and which introduces the preheated reaction mixture for starting the reaction.

Pressurized outer shell (1), in the center of its upper part, is equipped with a pipe (7) of large diameter which is suited for filling and emptying the catalyst, and a welded end (8) covers this pipe.

A catalysis space or chamber (10, 11, 11') is arranged inside the reactor and is concentric to the Pressurized shell, intended to receive the catalyst (9, 9', 9"). The non-removable space is inserted into the body of the reactor before the spherical end is welded (2'). This pipe (13), with the pipe (7) and, welded to casing (10), is equipped so that the bolts located diametrically opposite each provide a stationary point by support-clamping on the pressurized outer shell (1), thus distributing the longitudinal expansions while allowing vertical expansion to occur freely.

Inside the lower part of the space, or chamber 10 two gas collector pipes (16 and 16') are located, which are connected to the pipe of the effluent reactive gases (5').

In the central part of the reaction chamber (10), two removable internal partitions (17,18) and (17,18'), made up of two sectors of a circle which fit into each other, are arranged vertically to facilitate the insertion of the catalyst which is done through the pipe (7) and opening (12) starting at the ends, the removable internal partitions being registered. The catalyst, having been made level with the two plates (19) and (20) (FIG. 2) during filling, and taking into account the natural slope, arrives at the location of the internal partitions, whereupon the internal partitions (17) and (17') are raised, filling is continued, then internal partitions (18) and (19) are raised, the filling and levelling of the catalyst portions, (9) and (9') are completed, and then portion (9") is filled. Finally, the opening (12) is covered by cover (15) and the pipe (7) is covered by welding the end (8).

The thermal protection outer of the shell (1) is provided by heat insulation (39) located on the outside of the inner casing (10) and held by a series of Perforated circular ring supports 30a, two of which are shown by way of illustration in FIG. 1, In addition to its insulating qualities the type of heat insulation used also has good resistance to compression. The heat insulation takes on the function of supporting the catalyst-carrying enclosed space, which allows the elimination of all heat bridges between the inner casing (10) containing the catalyst and the perforated rings 30a holding the heat insulation (39). Furthermore, the outer shell (1) is also thermally protected by the circulation of protective gas (30), under pressure, which enters at 400° C. through pipe (3) and then reaches the interior of the catalytic chamber by internal pipe (3') located diametrically opposite it. This protective gas goes through the holes 30b, in the ring supports 30a and its circulation is piped, between the turns of a helically wound metal rod (40) into the space (31,32,33,34) located between the internal wall of the outer casing (1) and the hemispherical ends (2) and (2') and the external wall protecting heat insulation (39), concentric to the catalytic chamber.

At the start of the procedure, thermal protective gas (30) enters, the outer casing 1, 2, 2' under pressure, at (3) at 400° C. circulates in (31,32,33,34) and reaches, by connection (3'), the catalytic chamber at a temperature of nearly 400° C. in free zone (35) above the catalyst.

Synthesis gas (30'), first heated on the outside up to a maximum temperature of 500° C. for starting, enters the reactor by pipe (5), and mixes with the protective gas (30) in the space (35) between the upper surface of the catalyst and the internal wall of the catalytic chamber. The reaction mixture is divided at (36,37,38) in the distributor pipe for reagent gas, and goes through catalyst zones (9,9',9"). After reaction, the hot synthesis effluent (35',36',37,38') is collected in pipes (16) and (16') from which it again leaves by way of collector pipe (5') at a temperature of about 500° C., according to the operating conditions between 490° and 520° C.

In operation, after the start of the reaction, injection into (5) is stopped and only the synthesis gas, having played the role of protective gas (30), continues to circulate through passage (3') at a temperature of about 400° C. and then to enter at (35) into the catalytic chamber and pass over the catalyst, finally to leave again at (5') at a temperature of about 500° C. at the most.

Example 2

Horizontal single-layer reactor with a controlled wall temperature of a very moderate level, about 200° C.

The reactor shown in FIGS. 2, 3 and 4 of the accompanying drawing is a variant of the reactor described above as far as the structure of the circulation of the thermal protective gas and its temperature are concerned.

The body of the reactor consists of outer shell (1) with two hemispherical ends (2) and (2'). End (2') is equipped with a pipe (3) for introducing the fresh gas or the synthesis or protective gas at a temperature of about 200° C., which keeps the outer pressurized shell (1) at a very moderate temperature, with a pipe (4) forming a thermal casing and a box for the compensators (6') of the horizontal axial pipe for the discharge of the hot gas (5') after reaction at about 500° C.

End (2) is equipped with a pipe (3') for discharging the protective gas at a temperature a few degrees higher than the temperature of the inlet diametrically opposite pipe (3), with a pipe (4) which forms a thermal covering and a box for the compensators (6) of the inlet pipe (5) of the synthesis gas before reaction which is diametrically opposite the discharge pipe (5') of the hot gases after reaction.

As in the previous embodiment the outer, shell (1,2,2') is equipped with pipe (7) and welded end (8). Catalytic chamber (10,11,11') is located on the inside of the shell the chamber is equipped with an opening (12), a pipe (7), a casing (13), a flange (14) and a cover (15) having the same functions as in the reactor of example 1. The pipes (16 and 16') are arranged in the same way. And the catalytic chamber has removable internal partitions which fit into each other (17-18) (17'-18') with the filling of the catalyst (9,9',9") and its leveling at (19) and (20) being done according to the technique already described.

As before, the thermal protection of the body of force is provided by the same type of heat insulation (39). It is also provided by the circulation of protective gas (30) entering at 200° C. at (3) and leaving by way of pipe (3') at a temperature a few degrees higher. This circulation of the gas (30) is piped between the turns of the metal rod (40) in space (31,32, 33,34).

At the start of the process, the protective gas, having the composition of the synthesis gas, enters at (3) at a temperature of about 200° C., circulates in (31,32,33,34) and leaves at (3") at 200° C. This gas, first heated outside the reactor up to a maximum temperature of 500° C., enters by pipe (15) into the reactor, is piped through (35) and divided in the distributor pipe (36,37,38), and goes through catalyst zones (9,9',9"). After reaction, the hot gas which makes up the reaction effluent is collected by pipes (16,16'), from which it leaves by the collector ahead of pipe (5') at 500° C. maximum. During normal operation, after the start of the reaction, the same procedure is followed except that the entering synthesis gas is no longer preheated to 500° C. maximum, but is introduced at a temperature of about 400° C. into the catalytic chamber and leaves at a temperature of about 500° C.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

What is claimed is:

1. A reactor for catalytic synthesis under pressure comprising:
    an outer shell capable of being pressurized including a cylindrical wall with a main horizontal axis and having two hemispherical ends, and an inner shell concentric with said outer shell, defining an enclosed space for holding a catalyst;
    a single layer catalyst concentric with said inner shell and within said enclosed space, an external surface of said inner shell being covered with and supported by compression resistant insulation in contact therewith, a space being located between an internal surface of said outer shell and the covered external surface of the inner shell, protective perforated ring supports concentric with said inner shell enclosing said inner shell and supporting said insulation, said protective perforated ring supports having openings for the passage therethrough of gases, and a helical baffle wrapped about said inner shell, and extending from one end of said inner shell to the other, defining a generally horizontally disposed helical flow path for gases between said inner and outer shells, said helical flow path including said openings in said perforated ring supports;
    the outer shell and the inner shell being provided with means for introducing and withdrawing gas streams into said inner shell, located at the ends of the main horizontal axis of the reactor and facing each other on the hemispherical ends;
    the inner shell being connected to a vertical pipe for filling and emptying the catalyst.

2. A reactor according to claim 1, wherein the reactor includes a pipe for introducing reagent gas into the inner shell from outside the reactor, a pipe for removing effluent gas from the inner shell and passing said effluent gas outside the reactor, a distributor pipe for the reagent gas on the inside of the inner shell in its upper part, connecting to the pipe for introducing reagent gas and collector pipes for gas, located in its lower part, which are connected to the pipe for effluent gases.

3. A reactor according to claim 1, wherein the inner shell includes at least two removable vertical internal partitions made up of at least two sectors of a circle which fit into each other.

4. A reactor according to claim 3, wherein the insertion and withdrawal of the catalyst is done through an opening located in the upper part of the inner shell, said opening being a pipe welded to the pressurized outer shell, the pipe itself being equipped with a means for support clamping said pipe to said pressurized outer shell to provide a stationary point relative to longitudinal expansions, and said opening being covered by a welded cover.

5. A reactor according to claim 1, wherein the reactor is associated with at least one reactor of the same type or to at least one single-layer vertical reactor.

6. The reactor of claim 1, wherein said helical baffle is made of metal.

7. The reactor of claim 1, further comprising means for flowing gas from said flow path into said inner shell to mix with said reagent gas streams therein.

8. The reactor of claim 1, wherein said flow path remains independent from the gas streams in the inner shell.

9. In a process for synthesizing a gas selected from the group consisting of ammonia and methanol in a catalytic reactor by passing reactive pressure gases through said reactor, the improvement comprising the steps of;
    providing a reactor comprising a shell capable of being pressurized including a cylindrical wall with a main horizontal axis and having two hemispherical ends, and an inner shell concentric with said outer shell defining an enclosed space for holding a catalyst; a single catalyst concentric with said inner shell and within said enclosed space, an external surface of said inner shell being covered with and supported by compression resistant insulation in contact therewith, a space being located between an internal surface of said outer shell and the covered surface of the inner shell, protective ring supports concentric with said inner shell enclosing said inner shell and supporting said insulation, said protective ring supports having openings extending therethrough for the passage of gases, therethrough and a helical baffle wrapped about said inner shell and extending from one end of said inner shell to the other, defining a generally horizontally disposed helical flow path for gases between said inner and outer shells, said flow path including said openings of said ring supports; and
    passing a protective gas along said generally horizontally disposed helical flow path and through said opening in said support rings to prevent overheating of said outer shell.

10. The process of claim 9, wherein the reaction is conducted in the presence of a single layer of catalyst with reagent gases circulating vertically in the catalyst layer, wherein a stream of isothermal gas, lower in temperature than the gas contained in the catalyst-carrying internal enclosed space and made up of the feed gas under pressure before its introduction into the catalytic chamber, circulates on the outside of the catalytic chamber from one end to the other, thus providing thermal protection for the wall under high pressure.

11. A process for catalytic synthesis according to claim 10, wherein the thermal protective gas, under pressure, circulates in a helical fashion.

12. A process for catalytic synthesis of ammonia according to claim 11, wherein the thermal protective gas, under pressure, is introduced at the end of its circulation directly into the catalytic layer at a temperature between 370° and 420° C.

13. A process for catalytic synthesis of ammonia according to claim 11 wherein the thermal protective gas under pressure circulating at a temperature between 120° and 250° C. is heated on the outside at the end of its circulation before being reintroduced into the inner shell at the temperature level of entry into reaction.

14. A process for catalytic synthesis of ammonia according to claim 11, wherein the thermal protective gas, under pressure, is introduced at the end of said circulation, directly into the inner shell, at a temperature between 370° and 420° C.

15. A process for catalytic synthesis of ammonia, according to claim 14, wherein at the start of the reaction, a feed gas under pressure is introduced into the catalytic chamber at a temperature of at most 500° C., and during operating the temperature of the reagent gas when it enters the catalytic layer is about 400° C.

16. A process for catalytic synthesis of ammonia according to claim 14, wherein the thermal protective gas under pressure, circulating at a temperature between 120° and 250° C., is heated on the outside at the end of said circulation before being reintroduced into the inner shell at the temperature level of entry into reaction.

17. A process for catalytic synthesis of ammonia, according to claim 16, wherein in a starting phase, the reagent gas is composed of the mixture of a synthesis gas under pressure, first heated on the outside, and the isothermal protective gas under the same pressure as said synthesis gas.

18. A process for catalytic synthesis of ammonia, according to claim 17, wherein under normal operation, the reagent gas is composed only of the thermal protective gas.

19. A reactor for catalytic synthesis under pressure comprising:

a outer shell capable of being pressurized outer shell including a cylindrical wall with a main horizontal axis and having two hemispherical ends, and an inner shell concentric with said outer shell, defining an enclosed space for holding a catalyst;

a single layer catalyst concentric with said inner shell and within said enclosed space, an external surface of said inner shell being covered with a supported by compression resistant insulation in contact therewith, a space being located between an internal surface of said outer shell and the covered surface of the inner shell;

means defining a flow path for gases between said inner and outer shells and external to said insulation;

the outer shell and the inner shell being provided with means for introducing and withdrawing gas streams into said space between said outer shell and the covered surface of said inner shell, located at the ends of the main axis of the reactor and facing each other on the hemispherical ends;

the inner shell being connected to a vertical pipe for filling and emptying the catalyst.

20. The reactor of claim 19, further comprising means for flowing gas from said flow path into said inner shell to mix with said reagent gas streams therein.

21. The reactor of claim 19, wherein said flow path remains independent from the gas streams in the inner shell.

* * * * *